(12) United States Patent
Blakely et al.

(10) Patent No.: US 9,399,013 B2
(45) Date of Patent: Jul. 26, 2016

(54) STABLE AQUEOUS SUSPENSION

(75) Inventors: William Blakely, County Down (GB);
Louise Reynolds, County Down (GB);
Lillian Cromie, County Down (GB)

(73) Assignee: Norbrook Laboratories Limited,
Newry (GB)

( * ) Notice: Subject to any disclaimer, the term of this patent is extended or adjusted under 35 U.S.C. 154(b) by 894 days.

(21) Appl. No.: 12/301,053

(22) PCT Filed: May 10, 2007

(86) PCT No.: PCT/GB2007/001700
§ 371 (c)(1),
(2), (4) Date: Nov. 17, 2008

(87) PCT Pub. No.: WO2007/135362
PCT Pub. Date: Nov. 29, 2007

(65) Prior Publication Data
US 2009/0186883 A1 Jul. 23, 2009

(30) Foreign Application Priority Data

May 19, 2006 (GB) .................................. 0610058.0
May 23, 2006 (GB) .................................. 0610246.1
Apr. 30, 2007 (GB) .................................. 0708375.1

(51) Int. Cl.
*A61K 9/00* (2006.01)
*A61K 31/5415* (2006.01)

(52) U.S. Cl.
CPC ........... *A61K 9/0095* (2013.01); *A61K 31/5415* (2013.01)

(58) Field of Classification Search
CPC .................... A61K 9/0095; A61K 31/5415
See application file for complete search history.

(56) References Cited

U.S. PATENT DOCUMENTS

| | | | |
|---|---|---|---|
| 4,233,299 A | 11/1980 | Trummlitz et al. | |
| 5,183,829 A | 2/1993 | Caldwell | |
| 5,658,919 A | 8/1997 | Ratnaraj et al. | |
| 6,093,420 A * | 7/2000 | Baichwal | 424/468 |
| 6,184,220 B1 | 2/2001 | Turck et al. | |
| 6,794,411 B1 | 9/2004 | Lebon et al. | |
| 2002/0173497 A1 | 11/2002 | Ragunathan et al. | |
| 2004/0229038 A1* | 11/2004 | Cooper et al. | 428/402.21 |
| 2004/0258716 A1 | 12/2004 | Gao et al. | |

FOREIGN PATENT DOCUMENTS

| | | |
|---|---|---|
| CA | 2019863 | 6/1996 |
| EP | 0437258 | 7/1991 |
| EP | 0556057 A1 | 8/1993 |
| EP | 0843998 A1 | 5/1998 |
| EP | 1066029 B1 | 10/2002 |
| EP | 1520578 A1 | 4/2005 |

(Continued)

*Primary Examiner* — Trevor Love
(74) *Attorney, Agent, or Firm* — Porzio, Bromberg & Neuman P.C.

(57) ABSTRACT

An aqueous pharmaceutical suspension comprising: (i) at least one non-steroidal anti-inflammatory drug; (ii) an aqueous buffer system; (iii) xanthan gum; (iv) polyvinyl pyrrolidone; and (v) glycerol wherein the suspension is free from pregelatinized starch, amino polycarboxylic acid, microcrystalline cellulose, hydroxypropylmethyl cellulose, polyoxyethylene sorbitan monooleate, silicon dioxide and taste modifying agents selected from the group consisting of bulk sweeteners, intense sweeteners, flavoring agents and mixtures thereof.

9 Claims, 1 Drawing Sheet

(56) References Cited

FOREIGN PATENT DOCUMENTS

| | | |
|---|---|---|
| JP | 2000-119198 | 4/2000 |
| JP | 2000-136134 | 5/2000 |
| JP | 2005-041887 | 2/2005 |
| KR | 940003066 | 4/1994 |
| WO | 9949845 A1 | 3/1999 |
| WO | 03047502 A1 | 6/2003 |
| WO | WO 2006/061351 * 12/2005 | ......... A61K 31/5415 |
| WO | 2006061351 A1 | 6/2006 |
| WO | WO-2006/061351 | 6/2006 |

* cited by examiner

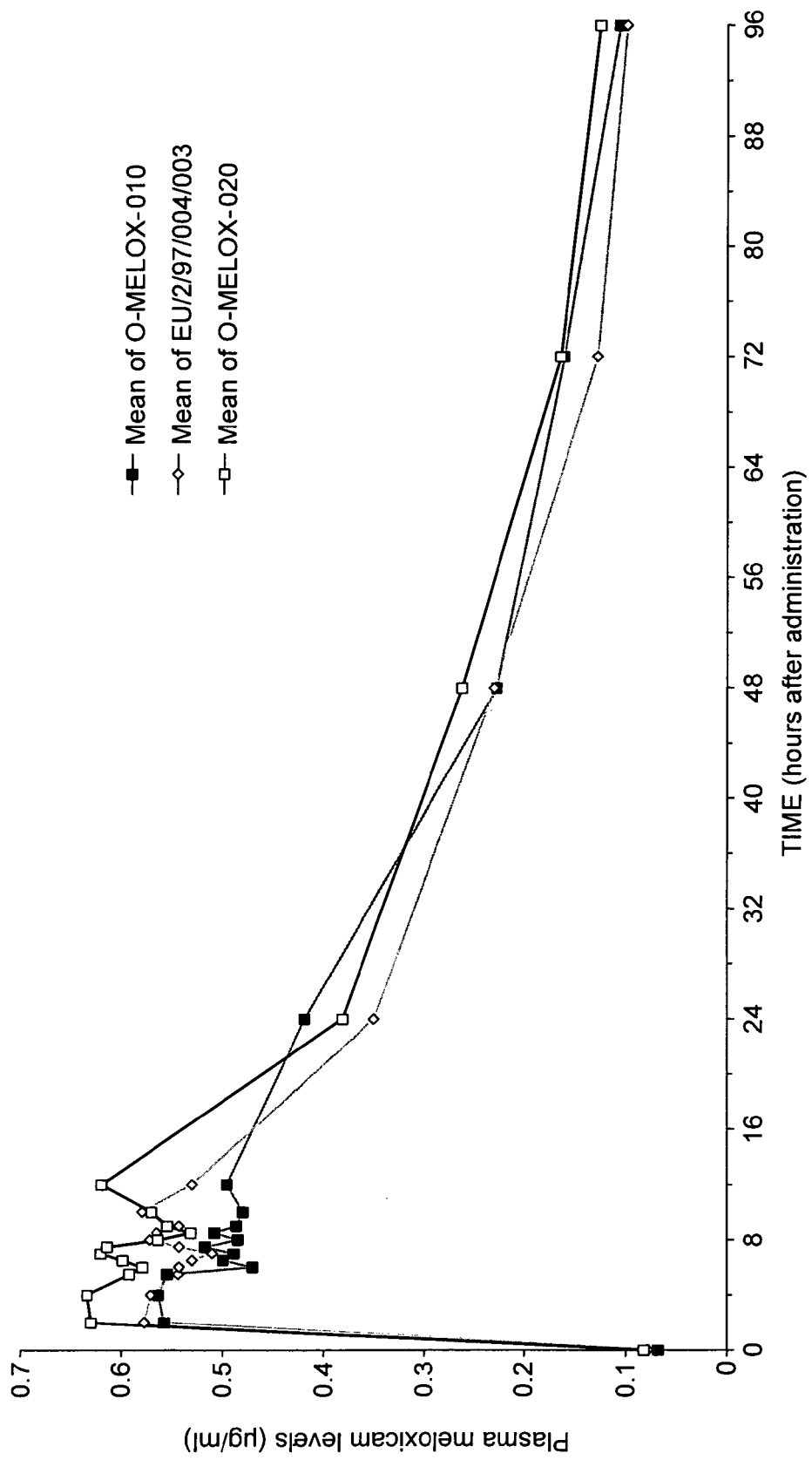

STABLE AQUEOUS SUSPENSION

The present invention relates to a novel aqueous pharmaceutical suspension for homogeneously suspending at least one non-steroidal anti-inflammatory drug, a method of their production and their use in the treatment of disease, especially inflammatory diseases in humans and animals.

Numerous pharmaceutically acceptable liquid suspensions are known in the art. Such suspensions are liquid systems having solid particles dispersed substantially throughout.

A common problem associated with liquid dosage forms, such as liquid suspensions, is the often disagreeable taste of a drug that manifests itself when the drug is in the liquid dosage form.

The prior art has shown extensive use of one or a combination of different flavouring methodologies to mask the unpleasant taste of drugs. For example, a flavour can be selected that complements the taste of the preparation, or a flavour with a longer intensity and stronger taste than the drug can be used. High levels of sweetening agents are often used to overwhelm bitterness with sweetness. The taste buds may also be anesthetized by menthol or mint flavours.

EP-A-1,066,029 (Metacam™) describes a complicated suspension for non-steroidal anti-inflammatory drugs that requires the presence of about 0.1 to about 5% by weight of a highly dispersed silicon dioxide and about 0.05 to about 2% by weight of a hydrophilic polymer. The suspension can further comprise a flavouring agent and/or a sweetener.

EP-A-1,520,578 further describes another suspension system for pharmaceuticals that comprises xanthan gum, a swelling agent, such as pregelatinised starch, a surfactant such as polyoxyethylene sorbitan monooleate, an amino polycarboxylic acid or salt thereof such as ethylenediaminetetraacetic acid (EDTA), and optionally a nucleation inhibitor, such as polyvinylpyrrolidone. Taste modifying agents, such as sugars, artificial sweetener, flavouring agents and mixtures thereof, can also be present and generally comprise 25 to 50% by weight of the total composition.

WO-A-2006/061351 further describes a suspension comprising meloxicam suspended in an aqueous glycerol mixture, a thickening agent, one or more taste modifying agents and a buffer system for maintaining the pH in a range from 2 to 4, wherein the suspension is free or essentially free of silicon dioxide.

As outlined above, the suspensions known in the art all rely on the presence of taste modifying agents such as bulk sweeteners, intense sweeteners, flavouring agents and mixtures thereof to mask the unpleasant taste of the drugs.

It has now been surprisingly found that a stable aqueous pharmaceutical suspension comprising a non-steroidal anti-inflammatory drug, an aqueous buffer system, xanthan gum, polyvinyl pyrrolidone and glycerol which is free from complex excipients such as pregelatinised starch, polyoxyethylene sorbitan monooleate, amino polycarboxylic acid like EDTA, microcrystalline cellulose, hydroxypropylmethyl cellulose, silicon dioxide and taste modifying agents selected from the group consisting of bulk sweeteners, intense sweeteners, flavouring agents and mixtures thereof can successfully mask the unpleasant taste of the drug that is present whilst maintaining stability over a long period of time and avoiding sedimentation of the non-steroidal anti-inflammatory drug.

Hence according to the present invention there is provided an aqueous pharmaceutical suspension comprising:
(i) at least one non-steroidal anti-inflammatory drug;
(ii) an aqueous buffer system;
(iii) xanthan gum;
(iv) polyvinyl pyrrolidone; and
(v) glycerol wherein the suspension is free from pregelatinised starch, amino polycarboxylic acid, microcrystalline cellulose, hydroxypropylmethyl cellulose, polyoxyethylene sorbitan monooleate, silicon dioxide and taste modifying agents selected from the group consisting of bulk sweeteners, intense sweeteners, flavouring agents and mixtures thereof.

The present invention further provides a process for the manufacture of the aqueous suspension as defined in any one of the preceding claims, comprising the following steps:
(i) dissolution of polyvinyl pyrrolidone in water;
(ii) dispersal of the non-steroidal anti-inflammatory drug in glycerol and in the polyvinyl pyrrolidone of step (i);
(iii) addition of xanthan gum to steps (i) and/or (ii);
(iv) making to volume with the addition of water; and
(v) mixing to bring the non-steroidal anti-inflammatory drug into a stable suspension.

In a preferred embodiment the non-steroidal anti-inflammatory drug is micronised prior to being introduced in step (i) and/or (ii).

In a further preferred embodiment paddle mixing is used in step (v) to bring the non-steroidal anti-inflammatory drug into a stable suspension.

The present invention provides the stable aqueous pharmaceutical for use as a medicament.

The present invention provides the use of the stable aqueous pharmaceutical suspension for the treatment of inflammatory or infectious diseases in humans and animals.

The present invention further provides the use of the stable aqueous pharmaceutical suspension for the manufacture of a medicament for the treatment of inflammatory or infectious diseases in humans and animals.

BRIEF DESCRIPTION OF THE FIGURES

FIG. 1 shows the mean plasma levels of meloxicam in dogs following oral administration at a dose rate of 0.2 mg meloxicam/kg bodyweight on 1 occasion.

For purposes of this invention, a suspension means a liquid system having solid particles dispersed substantially throughout. A suspension does not encompass emulsions which are meant to describe liquids suspended within liquid carriers or syrup formulations containing substantially fully dissolved pharmaceutical actives. As used herein, a "particle" may be a crystal, a granule, an agglomerate, or any undissolved solid material. At least 90% of the particles, preferably between 95 to 98% of the particles, have an equivalent diameter of less than 10 microns. The particle size is measured by laser diffraction.

One or more non-steroidal anti-inflammatory drugs can be selected from the group comprising of salicylates such as aspirin, methyl salicylate, Diflunisal and amoxiprin; acetaminophen; arylalkanoic acids such as diclofenac, indomethacin and sulindac; propionic acid derivatives (profens) such as ibuprofen, carprofen, naproxen and ketoprofen; N-Arylanthranlic acids (fenamic acid derivatives) such as mefanamic acid, meclofenamic acid and flufenamic acid; oxicams such as piroxicam, sudoxicam, isoxicam and meloxicam; coxibs such as celecoxib, rofecoxib, valdecoxib, parecoxib and etoricoxib; sulphonanilides such as nimesulide; and non-steroidal anti-inflammatory drugs that have both cyclo-oxygenase (II) and lipoxygenase inhibition properties such as tepoxalin and mixtures thereof.

The non-steroidal anti-inflammatory drug is preferably an oxicam, a propionic acid derivative or mixtures thereof. More preferably the non-steroidal anti-inflammatory drug is meloxicam, piroxicam, carprofen, ibuprofen, ketoprofen or mixtures thereof, more preferably meloxicam or carprofen and most preferably meloxicam.

At least 90% of the particles of the non-steroidal anti-inflammatory drug, preferably between 95 to 98% of the particles, have an equivalent diameter of less than 10 microns. The particle size is measured by laser diffraction. The particles of the non-steroidal anti-inflammatory drug having an equivalent diameter of less than 10 microns can be obtained for example by micronisation or by milling. Preferably the particles are obtained by micronisation.

The meloxicam is preferably meloxicam with 95 to 99% of particles having an equivalent diameter less than about 10 micron. Even more preferably the meloxicam particles having an equivalent diameter less than about 10 microns are obtained by micronisation.

The amount of non-steroidal anti-inflammatory drug present in the suspension should be sufficient to provide a therapeutic amount of the active and a convenient dosage unit. Accordingly, the at least one non-steroidal anti-inflammatory drug can be present in an amount of from about 0.1 to about 5% w/v of the suspension, preferably about 0.1 to about 2.5% w/v of the suspension, even more preferably about 0.1% to about 0.5% of the suspension, and most preferably in an amount of about 0.15% w/v of the suspension.

The non-steroidal anti-inflammatory drug can also be used in combination with other drugs such as but not limited to antimicrobials, antibiotics, antivirals, anti-ulcer/anti-acid agents and anti-cancer agents or a combination thereof.

The non-steroidal anti-inflammatory drug(s) are present in a "unit dose volume" of the aqueous suspension in a therapeutically effective amount, which is in an amount that produces the desired therapeutic response upon oral administration. In determining such amounts, the particular non-steroidal anti-inflammatory drug(s) being administered, the bioavailability characteristics of the non-steroidal anti-inflammatory drug, the dose regime, the age and weight of the recipient, and other factors must be considered, as known in the art. As used herein a "unit dose volume" of the aqueous suspension is a convenient volume for dosing the product to a recipient. The dosing directions instruct the recipient to take amounts that are multiples of the unit dose depending on for example the age or weight of the recipient. Typically the unit dose volume of the suspension will contain an amount of non-steroidal anti-inflammatory drug that is therapeutically effective for the smallest patient. For example, suitable unit dose volumes may include 0.2 mg non-steroidal anti-inflammatory drug/kg body weight.

The suspension can be dispensed from a suspension dispenser. The suspension is preferably foam free during dispensation from a suspension dispenser.

The pH of the suspension should range from about 3.5 to about 5, preferably from about 3.8 to about 4.2 and most preferably the pH of the suspension will be about 4. The suspension is buffered to maintain the pH of the suspension in the desired pH range. Suitable buffers that are not chemically reactive with the other ingredients may be present in an amount sufficient to provide the desired degree of pH buffering. Preferably the buffer is a sodium orthophosphate buffer or a citrophosphate buffer and most preferably the buffer is a sodium orthophosphate buffer.

The buffers can be present in an amount of from about 1 to about 4% w/v of the suspension, more preferably in an amount of from about 1.5 to about 2.5% w/v of the suspension.

Xanthan gum is a high molecular weight natural carbohydrate, specifically a polysaccharide. The xanthan gum is a viscosity increasing agent. Examples of suitable xanthan gums that can be used in the suspension include Rhodigel 80™, Keltrol™, Keltrol™ F, Keltrol™ T, Keltrol™ TF, Keltrol™ 1000 and Merezan™. Rhodigel 80™ is preferred.

The xanthan gum can be present in an amount from about 0.25 to about 1% w/v of the suspension, preferably from about 0.4 to 0.75% w/v and most preferably in an amount of about 0.4% w/v of the suspension.

The suspension includes polyvinyl pyrrolidone and glycerol. The polyvinyl pyrrolidone is acting as a dispersant and the glycerol as a vehicle density increaser.

The polyvinyl pyrrolidone can be present in an amount of from about 0.5 to about 10% w/v of the suspension, preferably from about 0.5 to 3.5% w/v of the suspension and most preferably in an amount of from about 1 to about 2.2% w/v of the suspension.

The glycerol can be present in an amount of from about 0.5 to about 50% w/v of the suspension, preferably from about 10 to about 30% w/v of the suspension and most preferably in an amount of about 15% w/v of the suspension.

The suspensions may also contain one or more of the following additives: preservatives, colourings, wetting agents, surfactants and electrolytes.

Preservatives that can be used in the suspensions include benzoic acid and its pharmaceutically acceptable salts, such as sodium benzoate; sorbic acid and its pharmaceutically acceptable salts, such as potassium sorbate; and parabens (such as methyl, ethyl, propyl and butyl p-hydroxybenzoic acids esters). Sodium benzoate is the preferred preservative.

The preservative can be present in an amount of from about 0.02 to about 0.5% w/v of the suspension, preferably about 0.1 to about 0.3% w/v of the suspension and most preferably in an amount of about 0.15% w/v of the suspension.

Colouring agents may also be incorporated in the suspension to provide an appealing colour to the suspension. The colouring agents should be selected to avoid chemical incompatibilities with the other ingredients in the suspension. Examples of suitable colouring agents include FD&C Red #40, FD&C Blue #1 and FD&C Red #33.

Examples of wetting agents which may be present include sodium lauryl sulphate or docusate sodium.

Examples of surfactants which may be present include sorbitan oleate ester or polyoxyethylene sorbitan fatty acid esters.

Examples of electrolytes which may be present include sodium chloride, potassium chloride or sodium bicarbonate.

In a preferred embodiment the stable aqueous pharmaceutical suspension is prepared by micronising the non-steroidal anti-inflammatory drug and then dispersing the micronised non-steroidal anti-inflammatory drug in glycerol. Polyvinyl pyrrolidone is dissolved in water to which the xanthan gum is added. This is then stirred until complete dispersion is attained. The non-steroidal anti-inflammatory drug is then added to the Polyvinyl Pyrrolidone/xanthan gum mix. To this aqueous buffer and aqueous sodium benzoate are added followed by water q.s. to 100%.

The suspensions can be used in the treatment of humans and animals against disease. In particular the suspensions can be used against inflammatory diseases such as arthritis or infectious diseases like those of the respiratory tract where inflammation plays a major part in the disease pathology.

The invention will now be described with respect to the following examples. The examples are not intended to be limiting of the scope of the present invention but read in conjunction with the detailed and general description above, provide further understanding of the present invention and an outline of a preferred process for preparing the suspensions of the invention.

EXAMPLE 1

The composition of the suspension of the current invention is provided in Table 1.

TABLE 1

Concentration of excipients an as a % of the w/v of Meloxicam suspensions Example 1a and Example 1b

| Excipient and Active content | Example 1a (% w/v) | Example 1b (% w/v) |
|---|---|---|
| Meloxicam (micronised) | 0.15 | 0.15 |
| Sodium benzoate | 0.15 | 0.15 |
| Glycerol | 15.0 | 15.0 |
| PVP | 1.0 | 2.2 |
| Rhodigel 80 ™ | 0.4 | 0.4 |
| Purified water q.s. to | 100 | 100 |
| Buffered | to a pH of 4 | to a pH of 4 |

Manufacture Process
Method for 2 L batch:
1) Micronisation of meloxicam.
2) Add 20 g of polyvinyl pyrrolidone to 1.5 L purified water and stir until dissolved.
3) Add 8 g xanthan gum to (2) and stir until completely dispersed.
4) Add 3 g micronised meloxicam to 300 g glycerol: and disperse by mixing with a high shear mixer.
5) Add (4) to (3) and disperse with high shear mixer.
6) Add the correct weight of buffer salts to 110 ml purified water and stir until dissolved.
7) Add (6) to (5) and mix.
8) Add 3 g sodium benzoate to 40 ml purified water and stir until dissolved.
9) Add (8) to (7) and mix.
10) Mix using a high shear mixer until homogeneous.
11) Check pH is in the range of from about 3.5 to about 4.5.
12) Dilute to 2 L with purified water and Silverson mix to homogenise.
Pharmacokinetics A pharmacokinetic study to determine the levels of meloxicam in dogs following the oral administration of the 2 formulations of Examples 1a, 1b and Metacam™ 1.5 mg/ml Oral Suspension for Dogs (Boehringer Ingelheim Limited, Marketing authorisation number EU/2/97/004/003) was carried out in order to compare the plasma levels of meloxicam following administration of the 3 articles. The pharmacokinetic parameters AUC (area under the concentration/time curve), $C_{max}$ (the maximum concentration), $T_{max}$ (time of maximum concentration), AUMC (area under the moment curve) and t½ (terminal half life) were determined.

Twelve dogs, six male and six female, at least 6 months of age and weighing between 10-15 kg bodyweight at the time of selection were used and were administered meloxicam at a nominal dose rate of 0.2 mg/kg bodyweight (approx. 1.0 ml article/7.5 kg bodyweight), by the oral route (using 2 ml syringes).

Blood samples were taken by venipuncture from the jugular vein. Immediately after collection samples were placed on ice prior to centrifuging and removal of the plasma. Samples were assayed singly for meloxicam concentration by HPLC.

The results from these trials are displayed in FIG. 1 (comparing Example 1a and Example 1b with metacam) with the actual data present in Table 1.

TABLE 2

Plasma levels of meloxicam (μg/ml) in dogs following oral administration of Example 1a, Example 1b and Metacam ™ 1.5 mg/ml oral suspension (EU/2/97/004/003) at a dose rate of 0.2 mg meloxicam/kg bodyweight

| Plasma Levels | Example 1a (n = 4) | Example 1b (n = 4) | Metacam ™ (n = 4) |
|---|---|---|---|
| Cmax (ug/ml) | 0.61 (+/−0.04) | 0.70 (+/−0.17) | 0.69 (+/−0.11) |
| Tmax (hours) | 5.38 (+/−4.72) | 6.88 (+/−4.13) | 6.50 (+/−3.42) |
| AUC (ug/ml hrs) | 26.82 (+/−2.24) | 28.98 (+/−6.38) | 25.43 (6.88) |
| AUMC (ug/ml hr^2) | 912.89 (+/−131.15) | 980.60 (+/−199.1) | 827.92 (+/−199.93) |
| MRT (hrs) | 33.94 (+/−2.31) | 33.95 (+/−1.15) | 32.78 (1.43) |
| T½ (hrs | 37.71 (+/−9.65) | 35.93 (+/−3.75) | 32.17 (+/−4.15) |

As is clearly evident from FIG. 1 as well as Table 2, Examples 1a and 1b show bioequivalence to Metacam™. There was also no adverse reaction to the taste or rejection of the suspensions by the dogs.

Furthermore it has surprisingly found that the suspension of this invention is substantially foam free during dispension from a suspension dispenser.
Stability The suspension properties of the suspensions of the current invention were evaluated against the current commercially available meloxicam oral suspension Metacam™.

To mimic the effects of age and transport on the suspensions, 32 ml samples of both products were centrifuged at 1448 g for 5 minutes. The suspension of the current invention maintained uniform suspension with no sedimentation or visible separation, however Metacam™ had 21 ml of clear supernatant.

The physical and chemical stability of the suspension of the current invention were tested at 25 degrees C. and 40 degrees C.

The results are as follows:
Results at time of manufacture:
Appearance: A pale yellow uniform suspension, no separation observed.
pH: 4.08 @ 25 degrees C.
Particle Size: 99%<10 micron
Meloxicam: 0.153% w/v
Results after storage (HDPE container 6 months at 40 Degrees C. and 75% RH:

Appearance: A pale yellow uniform suspension, no separation observed.
pH: 4.06 @ 25 degrees C.
Particle Size: 99%<10 micron
Meloxicam: 0.152% w/v Similar stability results were obtained using a 1% meloxicam suspension as well as with a 1% carprofen suspension.

EXAMPLE 2

A blind human taste test, comparing the composition of the suspension of the current invention as provided in Table 1 as Example 1a with Metacam™, was carried out.

The results are as follows:

| PRODUCT | TASTE | COMMENT |
| --- | --- | --- |
| Example 1a (n = 10) | Neutral | Agreeable |
| Metacam ™ | Very Sweet | Chalky film on tongue |

As illustrated there was no adverse reaction to the taste of the product.

The invention claimed is:

1. An aqueous oral pharmaceutical suspension comprising:
   (i) meloxicam;
   (ii) an aqueous buffer system;
   (iii) xanthan gum in an amount of 0.4% to 1.0% w/v of the suspension;
   (iv) polyvinyl pyrrolidone in an amount of 0.5 to 10% w/v of the suspension; and
   (v) glycerol in an amount of 0.5 to 50% w/v of the suspension;
   wherein the pH of the suspension is from about 3.5 to about 5 and wherein the suspension is free from pregelatinised starch, amino polycarboxylic acid, microcrystalline cellulose, hydroxypropylmethyl cellulose, polyoxyethylene sorbitan monooleate, silicon dioxide and taste modifying agents selected from the group consisting of bulk sweeteners, intense sweeteners, flavouring agents and mixtures thereof.

2. A suspension according to claim 1 wherein 99% of the meloxicam particles have an equivalent diameter less than about 10 micron.

3. A suspension according to claim 1 which further comprises a preservative.

4. A suspension according to claim 3 wherein the preservative is sodium benzoate.

5. A suspension according to claim 1 wherein the suspension is substantially foam free during dispensation from a suspension dispenser.

6. A suspension according to claim 1 wherein the suspension is stable at 40° C. for at least 6 months.

7. A suspension according to claim 1 further comprising at least one other drug.

8. A suspension according to claim 7 wherein the at least one other drug is an antimicrobial, antibiotic, antiviral, anti-ulcer/anti-acid or anti-cancer agent or a combination thereof.

9. A method for the treatment of inflammatory or infectious diseases in humans and animals which comprises administering the aqueous suspension of claim 1 to said humans and animals.

* * * * *